(12) United States Patent
Cohen

(10) Patent No.: US 7,153,298 B1
(45) Date of Patent: Dec. 26, 2006

(54) VASCULAR OCCLUSION SYSTEMS AND METHODS

(75) Inventor: Donald M. Cohen, Irvine, CA (US)

(73) Assignee: Vandolay, Inc., Irvine, CA (US)

( * ) Notice: Subject to any disclaimer, the term of this patent is extended or adjusted under 35 U.S.C. 154(b) by 284 days.

(21) Appl. No.: 10/401,846

(22) Filed: Mar. 28, 2003

(51) Int. Cl.
*A61B 18/18* (2006.01)
*A61B 18/22* (2006.01)

(52) U.S. Cl. ............... 606/12; 606/7; 606/11; 607/88

(58) Field of Classification Search ........ 606/4–7, 606/10–12; 607/88–92; 124/61, 62, 74–77
See application file for complete search history.

(56) References Cited

U.S. PATENT DOCUMENTS

| 5,344,418 | A |   | 9/1994  | Ghaffari |          |
|-----------|---|---|---------|----------|----------|
| 5,360,426 | A | * | 11/1994 | Muller et al. | 606/13 |
| 5,405,368 | A |   | 4/1995  | Eckhouse |          |
| 5,409,479 | A | * | 4/1995  | Dew et al. | 606/9 |
| 5,437,664 | A |   | 8/1995  | Cohen et al. |      |
| 5,643,252 | A | * | 7/1997  | Waner et al. | 606/9 |
| 5,778,868 | A | * | 7/1998  | Shepherd | 124/76 |
| 6,197,020 | B1 | * | 3/2001 | O'Donnell, Jr. | 606/9 |
| 6,306,130 | B1 | * | 10/2001 | Anderson et al. | 606/27 |
| 6,398,777 | B1 |   | 6/2002  | Navarro et al. |    |
| 6,599,256 | B1 |   | 7/2003  | Acker et al. |       |
| 6,666,856 | B1 | * | 12/2003 | Connors et al. | 606/9 |
| 6,918,762 | B1 | * | 7/2005  | Gill et al. | 433/29 |
| 2004/0010298 | A1 |   | 1/2004 | Altshuler et al. |  |

* cited by examiner

*Primary Examiner*—A. Farah
(74) *Attorney, Agent, or Firm*—Rutan & Tucker, LLP

(57) ABSTRACT

A blood vessel occlusion system and method includes a handheld probe including a power source, the probe being adapted to transmit energy from the power source through a body surface and into a target blood vessel, for example a varicose vein. Further included is a manual or automatic switch mechanism adapted to enable and disable the power source in response to a predetermined level of compression applied, by means of the probe against the target blood vessel. When the blood vessel is compressed sufficiently to collapse and substantially slow or substantially prevent a flow of blood therethrough, the power source is activated and the vessel is cauterized, leaving the blood vessel in a condition that is resistant to recanalization.

38 Claims, 5 Drawing Sheets

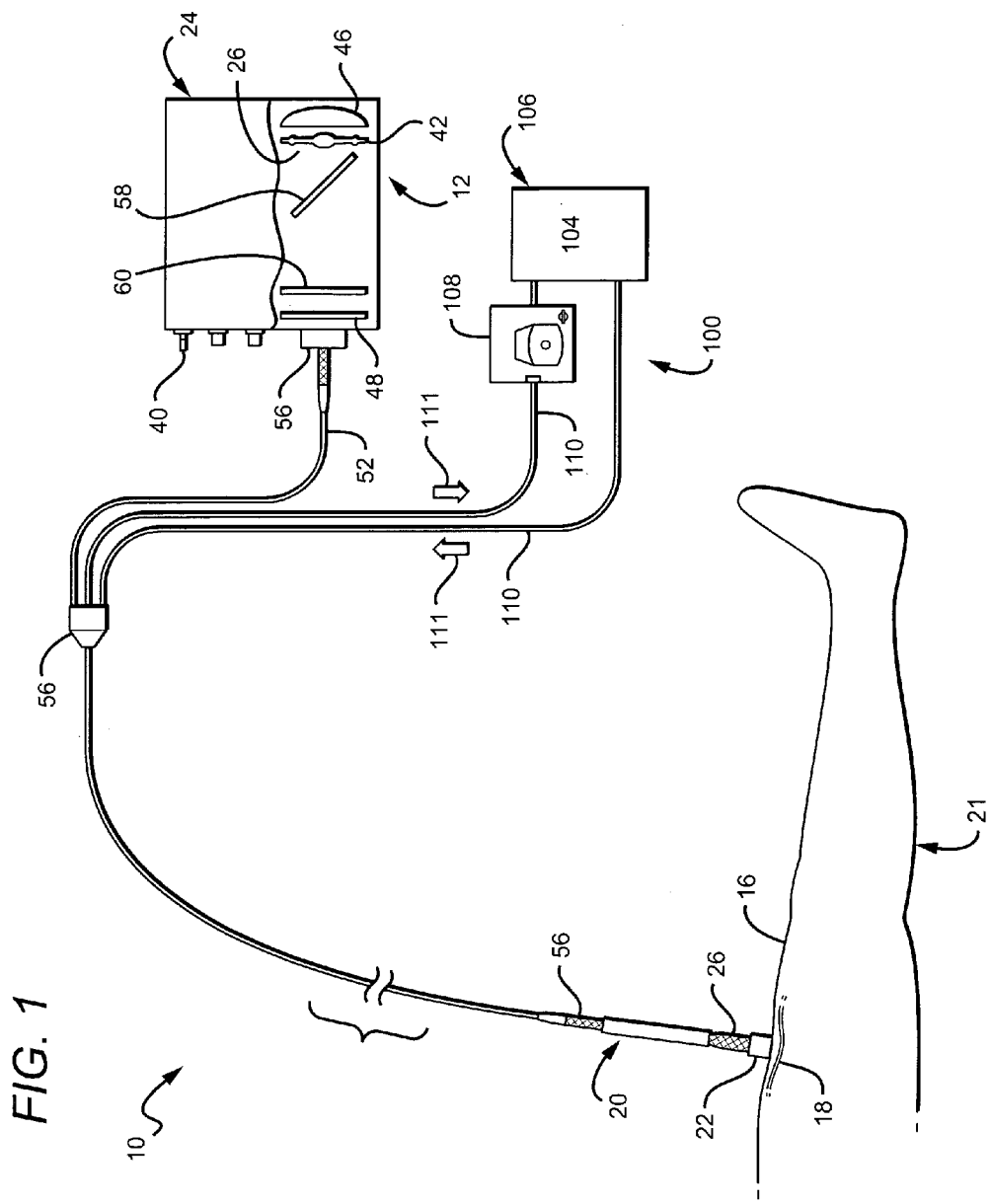

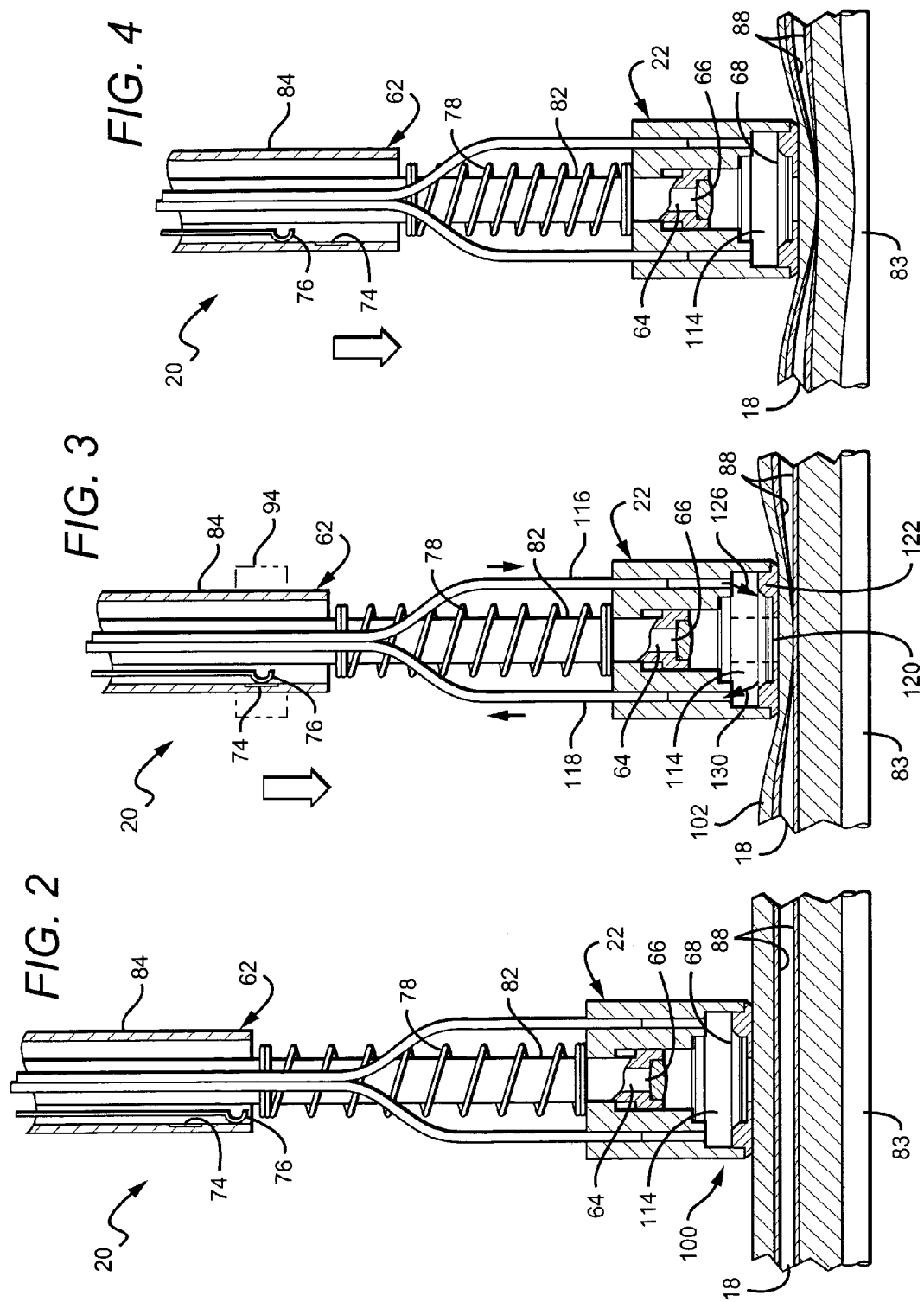

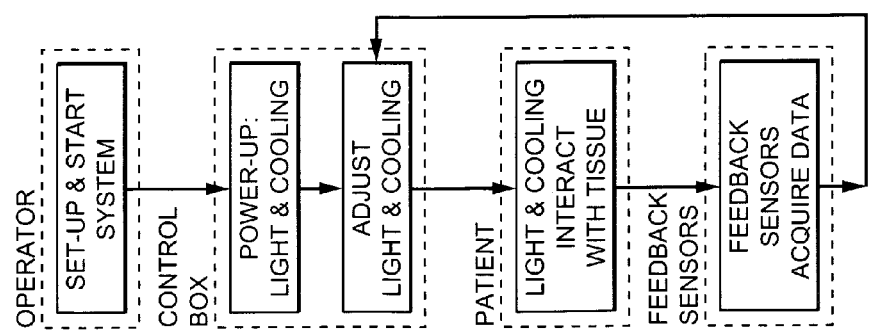

VASCULAR OCCLUSION SYSTEMS AND METHODS

BACKGROUND OF THE INVENTION

The present invention generally relates to medical apparatus and methods for medical and cosmetic procedures. More specifically, the invention relates to noninvasive apparatus and methods for occluding blood vessels, such as varicose veins.

There are a number of conditions in which there is a need to shut down and halt the circulation through particular blood vessels. Examples of blood vessels in which one may desire to reduce blood circulation include varicose veins, spider veins, hemangiomas, teleagectasias, hemorrhoids and gastric and intestinal bleeders.

Veins are vessels that carry blood back to the heart. There are a series of one-way, leaflet valves spaced throughout human veins. The valves form an integral portion of the skeletal pump which squeezes blood out of the veins whenever muscles contract. When functioning properly, the valves prevent blood from flowing in the retrograde direction (e.g., away from the heart) back into the vein portion upstream of the valve.

A varicose vein is recognized as a vein which has permanently lost its valvular efficiency and, as a result of continuous dilation under pressure, in the course of time, has become elongated and tortuous. Varicose veins occur frequently in the legs.

In many people, particularly women and those predisposed to the condition, the one-way leaflet valves within the leg vein often become dysfunctional and fail to seal completely. Thus, the portion of vein below the dysfunctional valve must support the weight of additional blood from the vein portion above the valve. The extra pressure increases the diameter of the vein, leads to additional valve leakage, visible varicose veins, and possible ulceration thereof.

In severe cases, varicose veins are treated by surgical excision, in which the vein is removed entirely from the body. The vessels to which the vein is joined are sealed, as with ligatures, at each attachment. The varicose vein is then cut and removed through incisions along the length of the vein. This process is documented to be at least a hundred years old.

A more recently developed, though similar technique is accomplished through a series of incisions, for example incisions of about 1–2 millimeters, along the vein. The target vessel (i.e., varicose vein) is then "hooked" with a stripping device and removed.

Rather than removing the vein, surgical repair of a varicose vein may be performed. Ligation or tying of the vein, through a small incision high in the leg vein, may be performed as a means of eliminating the source of pressure that distends the varicose vein. It is also known to apply a silicone band below the dysfunctional valve to cause narrowing of the valve.

Sclerotherapy is a technique that uses hypodermic needles to inject sclerosing agents into varicose veins to elicit clotting and ultimately scarring within veins to achieve venous occlusion. To treat large varicose veins, this technique requires the use of large volumes of, and/or highly caustic sclerosing agents. Such techniques carry risks of causing unintended thrombosis and embolization, among other things.

Noninvasive surgical procedures have also been developed for treating varicose veins. One such procedure utilizes an intense laser or pulsed broadband light source to treat veins between about 0.1 mm to 3 mm in diameter. These techniques are able to prevent the flow of blood through the veins by heating blood within the veins to form stable blood clots.

Noninvasive procedures for treating vascular disorders other than varicose veins have included the use of light to cause coagulation of small veins near the surface of the skin. For example, U.S. Pat. No. 5,405,368 entitled Method and Apparatus for Electromagnetic Treatment, discloses a method using high intensity, broadband incoherent light to noninvasively treat skin disorders. The pulse length of the light is selected to uniformly heat the entire thickness of the vessel as much as possible to achieve coagulation of the blood in the blood vessels. U.S. Pat. No. 5,344,418, entitled Optical System for Treatment of Vascular Lesion, discloses a system using a narrow band arc lamp for radiating light through a lens in contact with the skin, the peak wavelengths of the light being chosen to be absorbed by the blood to cause coagulation of the blood. A cooling mechanism is provided for protecting the skin from overheating.

In both of the above referenced patents, the disorders treated are small veins, i.e. veins of less than 0.5 mm in diameter. The target vessels may comprise port wine stains, telangiectasias, and cherry and spider angiomas. Although these conventional devices were developed for noninvasively treating vein abnormalities by heating, and coagulating blood by using light, it has not been suggested that the disclosed techniques would beneficial in treating larger vessels, such as varicose veins.

Percutaneous procedures have been used for treating varicose veins. U.S. Pat. No. 5,437,664 entitled Apparatus and Method for Venous Ligation, discloses the use of radio frequency power delivered via a device placed through a skin incision to shrink varicose veins. U.S. Pat. No. 6,398,777 entitled Endovascular Laser Device and Treatment of Varicose Veins, discloses the use of laser radiation delivered via an optical fiber placed through a skin incision to close varicose veins. These systems and methods require an incision to be made in the skin of the patient in order to treat the veins, and thus, provide a substantial risk of infection and require a healing period after the procedure.

There is still a need for simple, yet effective systems and methods for treating veins non-invasively without risk of injuring adjacent tissue. The present invention provides such systems and methods, described in detail below.

SUMMARY

New blood vessel treatment systems and methods have been invented. It has been found that application of sufficient, but not excessive, pressure against a vein section, for example a vein section recognizable as a varicose vein, during non-invasive transmission of energy into the compressed vein, will safely and permanently interrupt the blood flow through the section of vein and leave the vein in a condition that is neither visible by protrusion nor by discoloration, and is resistant to recanalization.

In short, apparatus and methods are provided specifically adapted and configured for this purpose. The present invention provides a cost efficient and straightforward treatment of blood vessels, such as varicose veins, with few, if any risks of injury to adjacent tissues or skin. Because the system is noninvasive and does not require even microsurgical incisions, there is almost no risk of infection to the patient, and a patient experiences a short recovery time. Because no materials are inserted or injected into the body, there is little risk of embolization and little risk of inadvertent ligation of other vessels. Furthermore, the present apparatus is designed with unique safety features that are developed toward reducing the level of guesswork required for safe and effective operation thereof.

The present invention is further distinguished from the prior art of non-invasive venous ligation treatment in the mode of lesion creation. Some prior art uses the transcutaneously transmitted power to heat the blood within the vessel to a temperature adequate to achieve thrombus formation; whereas the present invention uses the transcutaneously transmitted energy to heat the walls of the vessel adequate to achieve a stable closure of the blood vessel walls.

In one broad aspect of the present invention, a varicose vein treatment apparatus is provided which includes a handheld probe coupled to or including a power source for transmitting energy transcutaneously through a body surface and into a target blood vessel, for example a varicose vein. Further included is activating means for activating the power source in response to a predetermined level of compression applied against the target blood vessel. The activating means may be manually or automatically controlled. For example, if an operator determines that a desired amount of compression is being applied, a person, such as the operator, may activate the power source to apply energy to the target blood vessel. Alternatively, the activating means may be automated so that when a desired amount of compression is being applied, the power source is automatically activated to apply energy to the target blood vessel. The application of energy in the presence of moderate compression will promote the formation of a stable lesion and cauterization of the target vessel which is effective to occlude the flow of blood through the vessel.

Importantly, the predetermined level of compression is selected based on an amount of compression of the vessel that is sufficient for pressing the opposing inner surfaces of the blood vessel against each other, substantially slowing or substantially preventing a flow of blood through the target blood vessel. By positioning the opposing inner surfaces of the blood vessel in proximity to each other, energy provided by the power source is effective to join the opposing surfaces to each other to create an occlusion in the blood vessel. The occlusion may be sufficient to completely prevent blood flow through the blood vessel, or it may be sufficient to reduce the inner diameter of the blood vessel to reduce the amount of blood retrogradely flowing through the valve, and thereby reducing, and preferably eliminating, the varicosity.

Preferably, the power source is a device that is capable of generating sufficient energy to cause opposing sidewalls of a selected blood vessel to be effectively coupled together to reduce, and preferably prevent, the flow of blood through the blood vessel. The power source may be a source of electromagnetic radiation. In certain embodiments, the power source is a broadband light source. A useful broadband light source is a light source configured to emit radiation having a wavelength(s) in a range of between about 300 nm to about 2000 nm. In certain embodiments, the light source is configured to emit radiation in a range between about 300 nm and about 1100 nm. The power source may include a light source capable of emitting visible light, and/or near-infrared light. The power source may also include a laser. In additional embodiments, the power source may be a source of microwave energy configured to emit microwave energy having a frequency or frequencies in a range of between about 0.9 GHz to about 3 GHz. In other embodiments, the power source may be a device configured to emit radio frequency energy having a frequency or frequencies in a range from about 100 kHz to about 3 MHz. In still further embodiments, the power source may include an ultrasound device configured to deliver ultrasound energy to the desired blood vessel. In additional embodiments, the apparatus of the invention may include a combination of any of the foregoing power sources. The energy emitted by the power source may be delivered continuously, or the energy may be pulsed, or the energy may be gated. The energy may be gated by the actions of one or more shutter devices, and the like. Focusing means, such as an aiming lens, may be provided to concentrate the energy so that the power intensity is higher within the vessel than in the skin.

In one especially advantageous embodiment of the invention, the activating means for activating the power source includes a switch mechanism adapted to enable and disable the transmission of the energy. The switch may be operator controllable, or it may be automatically controlled. Preferably, the switch mechanism is further configured to enable the transmission of energy only when the applied compression against the target vessel is within a predetermined range. The apparatus is intended to cauterize the target blood vessel while the vessel is held in a collapsed state. The compression serves a multiple purpose by contributing to the efficiency and effectiveness of the cautery, the stability of a lesion formed thereby, and a desired cosmetic result.

More specifically, the switch mechanism is adapted to disable the transmission of the light when the applied compression is either too small or too great, i.e. inadequate or excessive. Preferably, the level of compression applied to the vessel is sufficient to cause contact between the interior vessel walls and substantially prevent blood flow therethrough. Even more preferably, the level of applied compression prevents blood flow but does not entirely eliminate the presence of a small amount or volume of blood remaining between the vessel walls. When a volume or aliquot of blood remains in the compressed portion of the blood vessel, the relatively high power absorption of the blood contained therein may enhance heat transfer into the vessel walls. This allows for the formation of a stable clot, stable vessel closure, and interruption of subsequent blood flow. In addition, it is important that the amount of applied compression is not excessive so as to interrupt blood flow in nearby arterial vessels.

An object of the present invention is to heat the opposing walls of the blood vessel as they are held in intimate contact with each other. When the constituents of the vessel walls are heated above the protein denaturization temperature, this presumably allows formation of new molecular bonds within the protein structures. Some of these new bonds effectively attach the one vessel wall to the opposing vessel wall. These bonds are believed to securely hold the vessel in the collapsed configuration.

The means for activating the power source in response to a predetermined level of compression may, for example, be comprised of a load cell within the apparatus that would enable functioning of the power source only when the load cell indicates that the applied pressure is within the desired range. Other means for permitting operation of the power source only when the pressure is within the desired range are contemplated. For example, electrical contacts within the probe may be provided, said electrical contacts being separated by a spring supported structure. More specifically, only when the spring is compressed within the desired range will the contacts overlap and thereby complete the electrical circuit to enable power to be delivered to the patient.

Means may also be incorporated to allow the focal point of the applied energy to be manipulated to create a seal across the entire width of a blood vessel. For example, a beam may have a cross-sectional diameter of about 1 mm. Because the cross-sectional size of the light beam is smaller than most of the veins being treated in accordance with this invention, this beam would be moved across the width of the varicose vein as the vessel is held in a compressed or collapsed configuration. Or, stated differently, a beam can have a region of minimum dimension, which may be an area of maximum intensity, the minimum dimension being about 1 mm. In addition, the beam need not be uniaxially symmetric. In certain embodiments, the beam may have a generally circular cross section, but in other embodiments, the beam has a rectangular or elliptical cross-section. Providing beams with non-circular cross sections provides an advantage of being able to create a cauterized line across the vessel, which may require less energy than a circular cautery zone does.

The present invention may further include an adjustment mechanism for adapting the apparatus to effectively treat the target blood vessel based on the size and/or depth of the vessel beneath the body surface. This could be accomplished by adjusting the enabling compression range to suit particular conditions. The size and depth of the vein may each act to change the pressure needed to collapse the vein. Thus, for example, a separate probe may be provided for treating each type of situation. Alternatively, the enabling range could be adjusted by changing the positions of the enabling electrical contacts within the probe, for example by a user manipulatable threaded collar having at least one of the electrical contacts mounted thereto.

It will be appreciated that alternative means for enabling adjustment of the apparatus to treat veins of varying sizes and conditions are contemplated. For example, the apparatus may include means for adjusting the waveband of light, to select a waveband that penetrates the body surface more deeply. Alternatively or additionally, a focal depth of the aiming lens can be adjusted. As yet another example, the amount of pressure for enabling transmission of light can be adjusted such that when a relatively low pressure is applied, only superficial or surface vessels will be collapsed and occluded in preparation for the cautery. In this respect, higher pressures will permit the collapse and subsequent treatment of deeper vessels.

Another advantageous feature of the invention is a cooling mechanism adapted to cool the body surface during the transmission of the energy, in order to prevent thermal damage to the skin and peripheral tissue. The cooling mechanism may comprise a cavity or chamber defined in a distal end region of the probe, wherein the cavity is adapted to contain a substantially transparent cooling medium, such as chilled water or other aqueous solution, for example. Thus, during operation of the apparatus, heat is conducted out of the superficial tissue and into the cooling medium. Preferably, the mechanism is adapted for circulating the water or other cooling medium to provide more effective, continuous cooling. A remote heat exchanger in fluid communication with the probe may be provided for removing heat from the circulating liquid.

In a preferred embodiment including the cooling mechanism, a liquid-free path is defined in the probe, which may comprise a liquid-free gap defined in the cooling medium cavity at the probe distal end region. Advantageously, this structure simplifies the optical path and therefore enables greater control over transmission of the light into the body surface. As an alternative means for simplifying the optical path, the cooling medium may be a gas rather than a liquid.

As a further advantage, the cooling may be provided by expansion cooling by allowing the ambient temperature gas to cool as it expands.

Any and all features described herein and combinations of such features are included within the scope of the present invention provided that the features of any such combination are not mutually inconsistent.

These and other aspects and advantages of the present invention will be more clearly understood and appreciated by reference to the following detailed description and claims, particularly when considered in conjunction with the accompanying drawings in which like parts bear like reference numerals.

BRIEF DESCRIPTION OF THE DRAWINGS

FIG. 1 is a perspective view of an embodiment of the present invention, including a varicose vein treatment handpiece, being used to treat a target blood vessel in a leg of a patient, the handpiece including a source of light for radiating the vessel as well as a means for activating the light source in response to a predetermined level of compression applied against the vessel.

FIG. 2 is a cut-away, partial cross-sectional view of the handpiece shown in FIG. 1, in which insufficient compression is being applied to the vessel such that the delivery of light is disabled.

FIG. 3 is a view of the same handpiece shown in FIG. 2, in which sufficient pressure is being applied to the vessel to enable delivery of light and effective treatment of the vessel.

FIG. 4 is a view of the same handpiece shown in FIGS. 2 and 3, in which excessive compression is being applied to the vessel such that delivery of the light is disabled.

FIG. 5 is a flow diagram of a method of the present invention for treating a varicose vein.

DETAILED DESCRIPTION

Figure 6A:
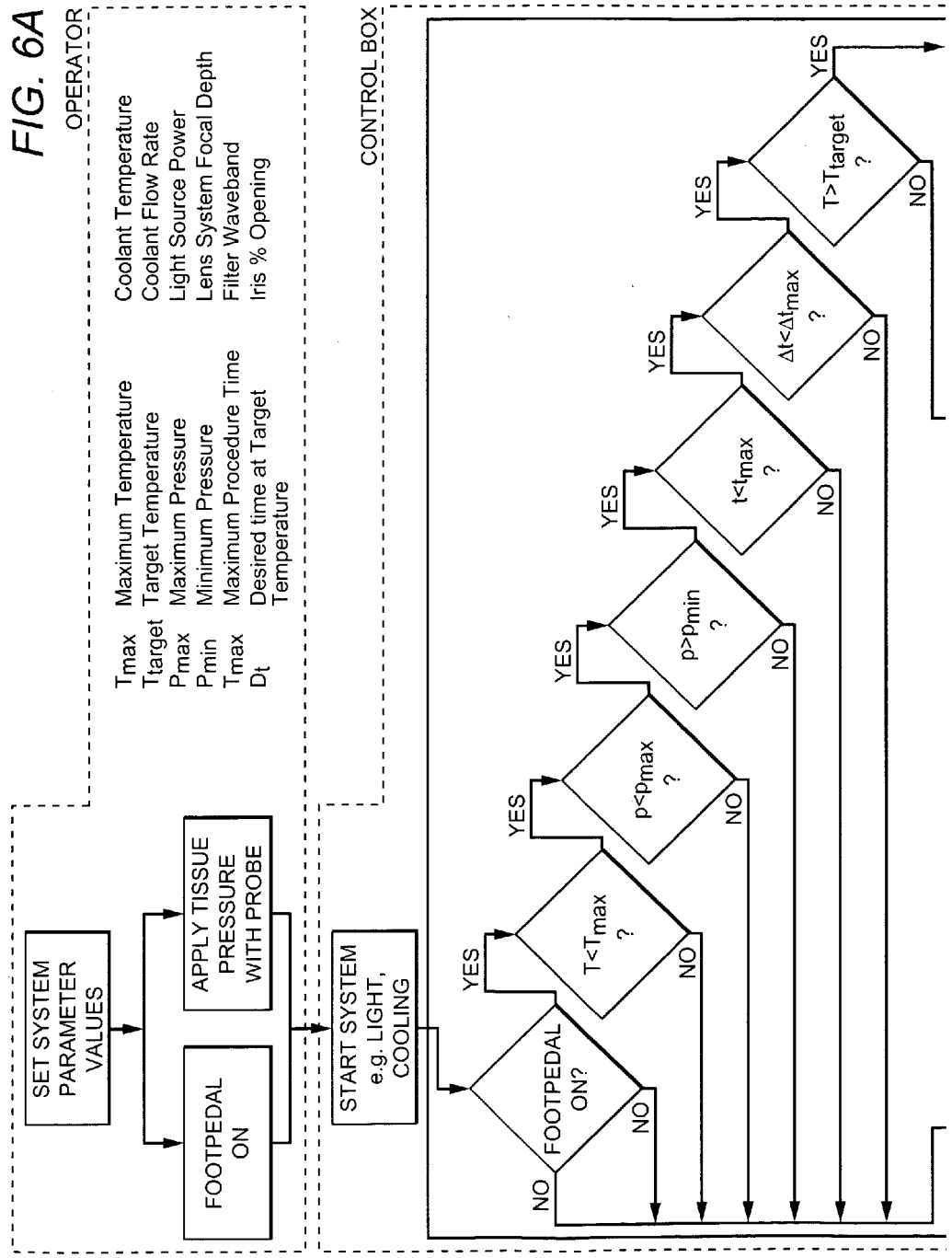
FIG. 6 is a more detailed flow diagram of the method of the present invention shown in FIG. 5.

Referring now to FIG. 1, a blood vessel treatment apparatus, in accordance with the present invention, is shown generally at 10, comprising a power source 12 for transmitting energy transcutaneously through a body surface 16 and in proximity to a target blood vessel 18, and preferably into target blood vessel 18, for example a varicose vein in a human leg 21. The apparatus 10 preferably includes a handheld probe, or handpiece 20, including a distal end region, hereinafter referred to as a probe head 22, for contacting the body surface 16, and a controller 24 operatively connected thereto.

As will be described in greater detail hereinafter, the source 12 of energy preferably includes an energy source configured to emit a sufficient amount of energy to couple two opposing sidewalls of a blood vessel together to occlude the flow of blood therethrough. In the illustrated embodiment, power source 12 includes a visible light source 26. It is to be appreciated, however, that with appropriate modification to the apparatus 10, different forms of energy may be utilized with the apparatus disclosed herein. Power source 12 may include, for example, a source of electromagnetic radiation, a source of microwave radiation, a source of radio frequency energy, and/or a source of ultrasound energy. In one embodiment, power source 12 includes a source of electromagnetic radiation, such as a light source configured to emit broadband light having a wavelength or wavelengths in a range from about 300 nm to about 2000 nm. In another embodiment, power source 12 includes at least one laser diode or light emitting diode (LED). In an additional embodiment, power source 12 includes a source of microwave energy configured to emit energy in a frequency range between about 0.9 GHz to about 3 GHz. In yet another embodiment, power source 12 includes a source of radio frequency energy emitted in a frequency range of between about 100 kHz and 3 MHz. A suitable source 12 of energy is capable of safely heating the blood vessel sufficiently to cause cauterization thereof.

The effectiveness of the wavelengths of energy chosen is dependent on several factors. Among these factors is the transmission of the energy wavelength through the intervening tissue of the patient, and the absorption of the energy by the target tissue. The most effective wavelength will be absorbed by the target blood vessel but will not be strongly absorbed by the intervening tissue. For example, when power source 12 is a light source, far infrared wavelengths may not be successful despite the strong absorption thereof by the vein and the blood, since far infrared wavelengths would also be strongly absorbed by the intervening tissue, such as the skin.

Visible light is reasonably well transmitted by the skin and reasonably well absorbed by the vein and blood. It has been shown that longer wavelengths of visible light can be more effective for deeper blood vessels. Since there is obviously a greater amount of intervening tissue when treating deeper veins, it is more important to utilize a waveband which would not be substantially attenuated by the intervening tissue.

Notably, when power source 12 is a light source, wavebands near the visible wavebands may also be advantageous. In particular, near infrared wavelengths are efficiently transmitted through the skin and subcutaneous tissue.

In the illustrated embodiment, a broadband light source 26 may be provided by a suitable lamp 42, for example a halogen lamp or an arc lamp as is known in the art, which is constructed to provide continuous high intensity visible light. An elliptical reflector 46 is shown adjacent the lamp 42. The light is passed through a focusing lens 48 and into means, for example an optical fiber (not shown), for transmitting the light to handpiece 20. More particularly, a suitable, conventional fiber optic cable 52 may be connected between the controller and handpiece 20 by suitable connectors 56 to the handpiece.

It is noted that instead of transmitting light though the fiber optic cable 52 into the handpiece 20 from a relatively remote lamp 42 (as shown and described herein), it is contemplated that the power source 12 may be substantially or entirely incorporated into the handpiece 20 in accordance with the invention. More generally, the power source 12 may be arranged in any suitable, conventional manner as known in the art.

In order to eliminate undesirable wavelengths or frequencies, for example far infrared wavelengths, the broadband light beam from the lamp 42 may be passed through one or more suitable filters (not shown) before being transmitted into the focusing lens 48. Alternatively, suitable reflectors may be provided. Shown in FIG. 1 is an infrared reflector 58 mounted between the lamp 42 and the lens 48.

There are other well known means in common usage for removing infrared wavelengths form broadband light sources. Notably mid and far infrared light are typically attenuated in fiber optic light cables. The light emerging from a fiber optic bundle, stripped of the infrared, is often referred to as a "cool light source." Typically, fiber optic bundles attenuate much of the far infrared light. Optical fiber material generally transmits visible and near infrared light best. In addition, water is commonly used as an infrared filter, since water transmits visible light more effectively than infrared light.

Dichroic beamsplitters are also frequently utilized to separate long from short wavebands. One waveband of a beam of broadband light is refracted through the beamsplitter while the other waveband is reflected by it. The desired wavelength is then directed toward an appropriate area. By using two dichroic beamsplitters, a particular waveband can be selected from the broadband light source. The beamsplitters may be dielectric coated glass intended to be used at a 45 degree angle to a beam.

Other means may be used to select wavebands. Cutoff wavelengths may also be adjusted by means well known in the art. For example, the generators of the power may be configured or adjusted to generate the desired frequency of energy.

Other suitable sources of electromagnetic radiation include lasers, laser diodes and LED's. Particularly in the case of the latter, an array of such miniature light sources may be employed to achieve the necessary power density in the varicose vein. The multiple light sources may be directed such that a point of convergence of light beams occurs beneath the skin within the varicose vein. To reduce the size of the probe, the light sources may be situated remotely, while optical fibers are used to convey the radiation to the target site.

It is noted herein that a "pulsed" light source, as is generally understood in the art, implies that power supplied to a lamp or bulb is pulsed. In other words, in a "pulsed" light source, the lamp or bulb will only emit light when an electrical pulse is applied thereto. In contrast, in a preferred embodiment of the present invention, a continuous light source is used. The light source is continuously illuminated during the treatment.

Although preferably the light source is continuously illuminated from the lamp 42, the present apparatus may further comprise a shutter mechanism 60 for gating the light, with an on-time of about 0.1 seconds to continuous, as it is being transmitted into the target vessel 18. In one embodiment, on-times of about three minutes have been demonstrated to be successful in occluding blood vessels.

Light interacts with the tissue as it enters the body surface 16. The light will be partially absorbed, partially transmitted and partially reflected. Ideally, the highest power density will occur in the blood vessel 18 and not in adjacent tissue. Preferably, means are provided for focusing the light from the handpiece and into the target blood vessel 18. The light may be focused directly from the source 12 toward the target tissue, or alternatively, may be relayed by a fiberoptic wave guide (not shown). The light may be focused by refractive or reflective optics, as is well known in the art. Reflective optics offer advantages of low losses and low wavelength dispersion.

An important aspect of the invention is the formation of a stable lesion in the vessel 18, resulting from the focused electromagnetic radiation, transmitted into the target vessel 18 while the vessel 18 is held in a collapsed state. This may be more clearly understood with reference to FIGS. 2, 3 and 4, which show the varicose vein treatment handpiece 20 in greater detail.

Specifically, a switch mechanism 62 or other suitable means are provided for activating the radiation source 12 in response to a predetermined level of compression applied against the target blood vessel 18. As indicated above, the switch mechanism may be controlled manually or automatically. Also as mentioned hereinabove but not shown in detail in FIG. 1, the radiation source may include an optical fiber 64. Shown in cut away view in FIGS. 2–4, is a distal end region 66 of the optical fiber 64 for radiating light through a focusing lens 68 into the target blood vessel 18.

As a specific example, though not intended to limit the scope of the present invention, the switch mechanism 62 may include first and second electrical contacts 74, 76 respectively, disposed within the handpiece 20, the contacts 74, 76 being biased apart, and not in contact with one another, by means of a spring 78 or the like.

Thus, only when the spring 78 is compressed within a desired range, do the contacts 74 and 76 overlap and therefore complete an electric circuit, enabling the transmission of radiation into the blood vessel 18. The handpiece 20 may include inner member 82 housing the optical fiber 64. A shell or outer housing 84, sized to be held in one hand by an adult human being (not shown) is slidably mounted with respect to the inner member 82. The probe head 22 is mounted to the inner member 82 and provides means for contacting the body surface 16.

In practicing a method of the present invention, an operator (not shown) applies manual compression of the handpiece 20 against the body surface 16. This causes the outer housing 84 to slide downward, against the spring 78, bringing the second contact 76 closer to the first contact 74. Only when the contacts 74, 76 meet will light be delivered to the handpiece 20, signifying that adequate but not excessive compression is being applied to the vessel 18.

In another embodiment not shown, the compression is applied by one or more compression devices attached to or otherwise located on the patient. The compression devices may include, among other things a pneumatic cuff or an elastic band. These compression devices apply the correct compression to hold the vessel in the desirable collapsed condition.

FIG. 2 shows the handpiece 20 contacting the body surface 16, but little or no compression is being applied thereto. As shown, the electrical contacts 74 and 76 are apart, disabling the delivery of light into the vessel 18.

FIG. 3 shows the handpiece being pressed against the body surface 16 with sufficient force to collapse the vessel 18. Delivery of light is enabled by the contacts 64 and 66 completing the circuit. In FIG. 3, the collapsed vessel 18 is being radiated with and heated by the light, causing cauterization of the vessel 18.

FIG. 4 shows the handpiece as being pressed against the body surface 16 with excessive force. As shown, the excessive force has not only caused collapse of the target blood vessel, i.e. the varicose vein 18, but has also caused collapse of a deeper, non-target vessel 82 and other non target vessels which could otherwise cool the skin and protect it from being burnt. The second electrical contact 76 has traveled past the first electrical contact 74, and thus, delivery of light has been disabled, preventing injury to non-target tissue.

As an example, the first contact 74 may be a cylindrical band of electrically conductive material fixed within to an internal wall of the housing 78. The second contact 76 may be an electrically conductive leaf spring.

Importantly, the predetermined level of compression is sufficient to substantially slow, or substantially prevent, a flow of blood therethrough. More specifically, the compression against the target blood vessel 18 is sufficient to cause inner walls 88 of the vessel 18 to contact one another as shown in FIG. 3.

Alternative means of compressing the vessel within a desired range are contemplated and are considered to be within the scope of the present invention. Means may also be provided for monitoring the level of compression applied against the vessel 18. For example a small load cell could be incorporated within the probe head 86. Logic within the instrument 20 would enable functioning of a physician operated switch (not shown) when the load cell indicates that the applied pressure is within the desired range.

Preferably, the enabled pressure range is adjustable for various conditions. For example, size and depth of the target blood vessel 18 may effect the compression needed to adequately collapse the vessel 18. Means may be provided for enabling selection of the enable pressure range. For example, a separate handpiece may be made available for each range. Alternatively, the enable pressure range may be adjustable by changing location of the first or second contact 74, 76 within the probe. More specifically, the first contact 74 may be mounted on a user manipulatable threaded collar 94 (shown in phantom line in FIG. 3) within the handpiece 20.

Other means of adjusting the instrument for veins of various depths and sizes are contemplated. For example, since longer wavelengths of light will tend to penetrate the body surface more deeply, the waveband may be adjusted to target blood vessels at different depths. Alternatively, or additionally, the focal depth of the aiming lens, and/or the beam dimensions can be adjusted using conventional means. The amount of pressure to enable transmission of power can be adjusted such that when a lower pressure is used only superficial vessels will be ligated, while higher pressures still permit ligation of deeper vessels as well.

It is noted again that preferably, the flow of blood through the vessel is substantially stopped during the application of the light, otherwise the flowing blood will tend to carry away much of the heat. In other words, the flowing blood may continue to cool the vein at the same time the light source is applying heat to close the vein.

However, the presence of a small amount of blood between the collapsed walls is acceptable and desirable, as long as the flow has substantially ceased. The volume or aliquot of blood present in the collapsed vein will absorb a fraction of the light, thereby forming a stable clot which will maintain interruption of subsequent blood flow and prevent or reduce a chance of recanalization of the vessel 18. When the vessel walls 88 are held in contact as hereinabove described, the stability of the resulting lesion is much greater than mere clot formation by heating alone. In other words, a more stable closure is achieved by cauterizing the vessel while opposing surfaces are held in apposition.

It is important that a good cosmetic result is achieved. A large blood clot "cord" or a bumpy skin surface resulting from the procedure would be unsatisfactory. Thus, again, it is important to exclude most blood from the vessel while the cautery is taking place.

Advantageously, referring now to both FIGS. 1 and 3, the present invention may further comprise a cooling mechanism 100 adapted to cool the body surface 16 during transmission of the electromagnetic radiation.

Light is passed through skin and subcutaneous tissue 102 before it reaches the vein 18 to be cauterized. Ideally, this intervening tissue 102 would absorb insubstantial amounts of light and thus the temperature of the tissue 102 would not rise appreciably. However, the intervening tissue 102 may absorb significant portions of the light which in the absence of cooling could possibly causing blistering or other thermal damage. The cooling mechanism 100 is provided to cool these structures 102. One means of achieving effective cooling is to conduct heat away from the body surface 16 through the probe head 22.

For example, the cooling mechanism 100 may include a circulation assembly for circulating a cooling fluid comprising a suitable medium such as clear water, between a fluid source 104 and the probe head 86. As shown in FIG. 1, the fluid source 104 may include a remote heat exchanger 106 adapted to remove heat from the cooling fluid passed from the handpiece 20. A peristaltic pump 108, or the like, may provide means for circulating the fluid, for example in a flow direction represented by arrows 111 through a fluid conduit 112 connected between the heat exchanger 106 and the handpiece 20.

Turning now specifically to FIG. 3, a cooling medium cavity, or chamber 114 is defined in the handpiece 20 adapted and positioned to effectively remove heat from the body surface 16 during the treatment in order to prevent thermal injury to the patient. As shown, the cooling chamber 114 includes coolant supply tube 116 and coolant exhaust tube 118, in fluid communication with the coolant conduit 112, and defining inlet 126 and outlet 128, respectively, for allowing the cooling fluid to pass through the cooling chamber 114.

The probe head 86 may include a thin, clear glass window 120 centered by means of a heat conducting flange 122, such as a metal flange. This structure promotes rapid and continuous conduction of heat from the tissue and into the probe head 22. The window may be constructed of other thin clear materials such as acetate, polyethylene or sapphire.

Preferably the thickness of the cooling chamber 114 is kept thin to reduce optical attenuation.

In a preferred embodiment including the cooling mechanism, a liquid-free path is defined in the handpiece, which may comprise a liquid-free gap 128 shown in phantom line in FIG. 3, defined in the cooling medium cavity in the probe head 86. In other words, the cooling medium cavity 114 may be substantially donut shaped. Advantageously, this structure simplifies the optical path and therefore enables greater control over transmission of the light into the body surface 16.

As an alternative means for simplifying the optical path, the cooling medium may be a gas rather than a liquid. It is contemplated that the gas could cool the probe head 22 and the tissue primarily by expansion cooling. For example, as the gas is allowed to expand in the probe head 86, heat will be absorbed therefrom, thereby cooling the tissue 102. One or more refrigerants known in the art could also be used for this application. For example, low molecular weight non-toxic organic gases are used in certain embodiments to achieve the desired cooling. In other embodiments, cooling could be obtained by expansion cooling methods, by using compressed air, which is not necessarily liquefied air. As yet another alterative, the cooling could be achieved by a thermoelectric generation, i.e. the Seebeck effect, as will be understood by those familiar with the art.

Figure 6B:
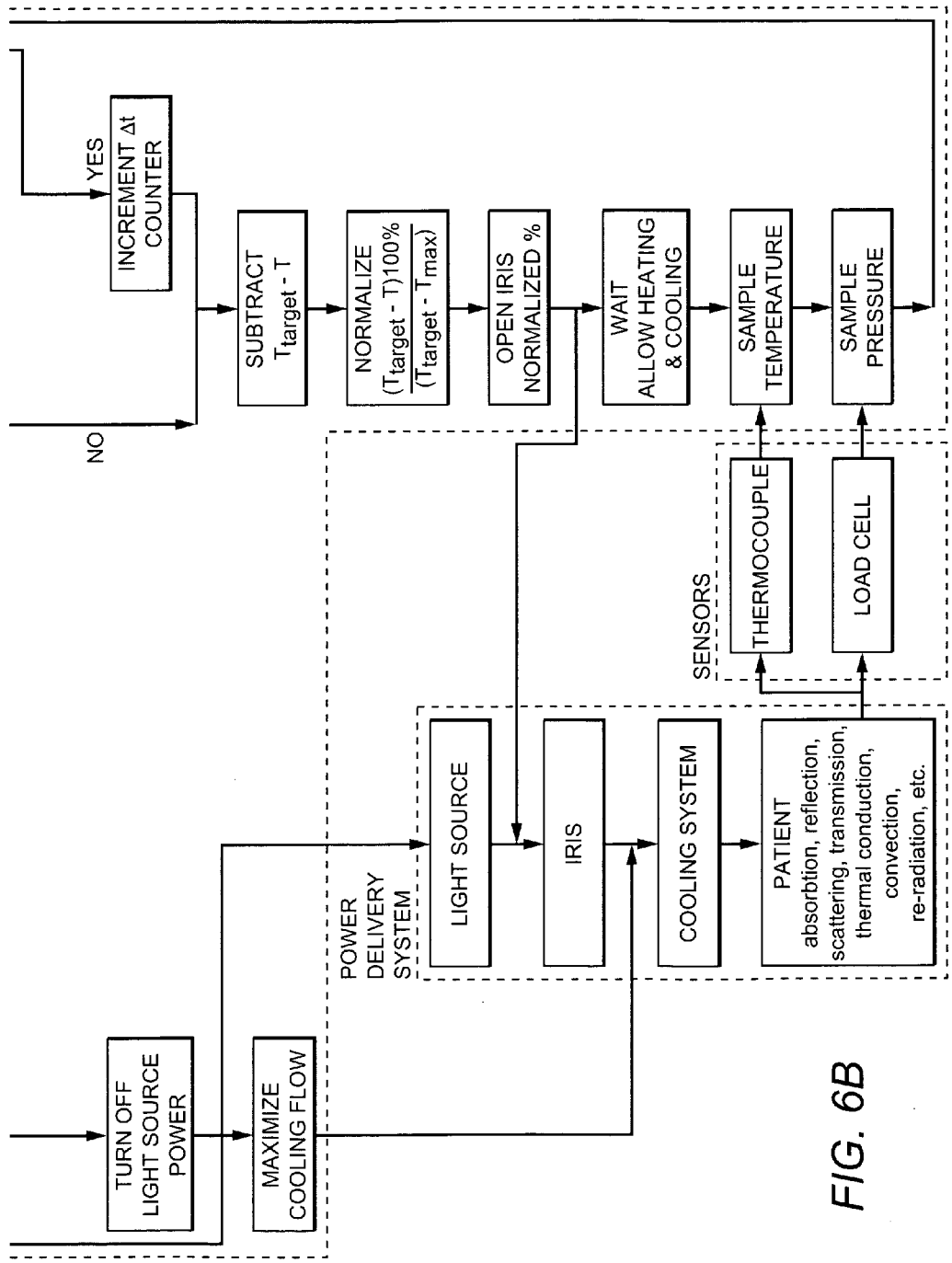

The apparatus herein above described is suitable for performing a method in accordance with the present invention for occluding a blood vessel, such as a varicose vein, the method generally comprising the steps described in detail herein above. FIG. 5 shows a simple flow diagram of a method of the present invention for treating a varicose vein. FIG. 6 is a more detailed flow diagram of the method of the present invention shown in FIG. 5.

In a preferred embodiment, the application of energy and compression are applied for a duration known to safely and effectively occlude a varicose vein. The amount of energy, compression, and the duration of each are preferably determined by the operator of the apparatus of the invention, and will vary depending on person being treated.

In an additional embodiment there will be feedback control to reduce the possibility of inadvertent thermal damage. The control may be comprised of any suitable means, including safety and efficacy features. For example, it is preferable to monitor the temperature of the vessel while it is being treated. Since the procedure is preferably non-invasive, monitoring of the temperature may be estimated by the empirically measured relationship between surface temperature and subcutaneous temperature for the particular heating time and rate and cooling time and rate. A miniature thermocouple or other temperature sensor, may be incorporated to monitor temperature at the skin surface adjacent to the region of treatment or to monitor the temperature of a cooling mechanism of the apparatus.

Feedback of skin temperature may be relayed to the controller which would automatically adjust either the heater power or the cooling to keep the temperature within a desired range for a desired time.

Pressure applied to the vessel, as mentioned briefly hereinabove may be monitored, and feedback data relayed to the controller. Pressure monitoring may be accomplished by incorporating within the system a load cell or pressure transducer or other monitoring means known in the art. Formation of the lesion induced by the apparatus of the present invention can also be monitored and measured, using for example reflection measurements made at two wavelengths to yield a ratiometric measurement. As a lesion is generated in the treated vessel, the reflection signal from venous blood should decrease while the reflection signal from clot and lesion will increase. These measurements may be made transcutaneously as is well known in the art. In additional embodiments, a spectroscopic sensor may be provided to monitor the procedure and the generation of the blood vessel occlusion.

While this invention has been described with respect to various specific examples and embodiments, it is to be understood that the invention is not limited thereto and that it can be variously practiced within the scope of the following claims.

What is claimed is:

1. An apparatus capable of occluding a varicose vein that underlies living skin and has a diameter of at least 0.5 mm, the apparatus comprising: a handpiece having an energy emitter and a trigger that initiates release of energy from the emitter through the skin and into the vein, as a function of detection of a pressure at the handpiece sufficient to cause deformation of the skin and to collapse the vein, and where the energy has sufficient intensity and duration to permanently close juxtaposed walls of the vein without perforating the skin.

2. The apparatus of claim 1 further including a power supply external to the handpiece that provides power to the emitter.

3. The apparatus of claim 1 further including a power supply internal to the handpiece that provides power to the emitter.

4. The apparatus of claim 1 wherein the energy emitter emits a wave of electromagnetic radiation.

5. The apparatus of claim 1 wherein the electromagnetic radiation includes at least some near infrared wavelengths.

6. The apparatus of claim 1 wherein the energy emitter emits a particle beam.

7. The apparatus of claim 1 wherein the energy emitter emits a sound wave.

8. The apparatus of claim 1 further comprising a fiber carried by the handpiece that transmits waves to the energy emitter.

9. The apparatus of claim 1 wherein the emitter has a focusing element that has a focal length of at least 0.5 nm beyond an end of the handpiece.

10. The apparatus of claim 1 wherein the emitter has a focusing element that produces a focus area having a non-circular shape.

11. The apparatus of claim 1 wherein the headpiece further includes a displacement sensor to determine the pressure.

12. The apparatus of claim 1 wherein the handpiece further includes a pressure sensor to determine the pressure.

13. The apparatus of claim 1 wherein the handpiece further includes a sensor other than a displacement sensor or a pressure sensor to determine the pressure.

14. The apparatus of claim 1 further included a user-operated safety cutoff that restricts a function of the trigger.

15. The apparatus of claim 1 further including a controller that alters an emission parameter of the energy emitter.

16. The apparatus of claim 15 wherein the emission parameter includes a level of intermittency.

17. The apparatus of claim 15 wherein the emission parameter includes automatic attenuation of an intensity of the energy to a non-zero level during a course of treatment.

18. The apparatus of claim 15 wherein the emission parameter includes automatic adjustment of an intensity of the energy during a course of treatment as a function of progress of the treatment.

19. The apparatus of claim 15 wherein the emission parameter includes automatic adjustment of an intensity of the energy during a course of treatment as a function of a temperature at a treatment site.

20. The apparatus of claim 15 wherein the emission parameter comprises a time duration between determination of the pressure and release of energy from the emitter.

21. The apparatus of claim 15 wherein the emission parameter comprises a time duration of emission of energy from the emitter.

22. The apparatus of claim 15 wherein the emission parameter comprises a relative sequence of determination of the pressure and release of energy from the emitter.

23. The apparatus of claim 15 wherein the emission parameter comprises a beam intensity.

24. The apparatus of claim 1 further comprising a feedback loop that interrupts emission of energy upon determination of an adverse condition.

25. The apparatus of claim 24 wherein the adverse condition comprises a safety problem.

26. The apparatus of claim 25 wherein the safety problem comprises an overheating of a portion of skin of a patient.

27. The apparatus of claim 24 wherein the adverse condition comprises an efficacy problem.

28. The apparatus of claim 27 wherein the efficacy problem comprises a determination of insufficiency in the pressure.

29. The apparatus of claim 27 wherein The efficacy problem comprises a mal-position of the emitter with respect to the vein.

30. The apparatus of claim 1 wherein the pressure comprises a force imparted to an end portion of the handpiece.

31. The apparatus of claim 1 wherein the pressure comprises a force imparted to the handpiece by a hand of a user.

32. The apparatus of claim 1 further comprising a cooling element that at least partially offsets a superficial heating effect caused by the emitter.

33. The apparatus of claim 32 wherein the cooling element is mechanically coupled to the handpiece.

34. The apparatus of claim 32 wherein the cooling element uses a liquid coolant.

35. The apparatus of claim 32 wherein the cooling element uses a gaseous coolant.

36. The apparatus of claim 32 further comprising a controller that alters a flow of a coolant as a function of progress of a treatment.

37. The apparatus of claim 1 further comprising a first controller that alters an emission parameter of the energy emitter, and a second controller that alters a flow of a coolant as a function of progress of a treatment.

38. The apparatus of claim 1, wherein the handpiece is sized and dimensioned to trap a volume of fluid in the vein.

* * * * *